United States Patent [19]
Peet et al.

[11] Patent Number: 5,252,565
[45] Date of Patent: Oct. 12, 1993

[54] HALOETHYL-SUBSTITUTED STEROID ENZYME INHIBITORS

[75] Inventors: Norton P. Peet, Cincinnati; J. O'Neal Johnston, Milford; Joseph P. Burkhart, West Chester, all of Ohio

[73] Assignee: Merrell Dow Pharmaceuticals Inc., Cincinnati, Ohio

[21] Appl. No.: 755,710

[22] Filed: Sep. 6, 1991

Related U.S. Application Data

[63] Continuation-in-part of Ser. No. 503,191, Apr. 2, 1990, abandoned.

Foreign Application Priority Data

Mar. 25, 1991 [CA] Canada .................. 2038985

[51] Int. Cl.$^5$ .................. A61K 31/56; C07J 1/00
[52] U.S. Cl. .................. 514/177; 514/178; 514/182; 552/526; 552/615; 552/632; 552/650; 552/651
[58] Field of Search .............. 552/632, 651, 615, 650, 552/526; 514/177, 178, 182

[56] References Cited

U.S. PATENT DOCUMENTS

| | | | |
|---|---|---|---|
| 3,121,079 | 2/1964 | Oberster et al. | 552/642 |
| 3,138,623 | 6/1964 | Bergstrom | 552/646 |
| 3,207,753 | 9/1964 | Bowers et al. | 552/642 |
| 3,284,448 | 11/1966 | Cross | 552/632 |

FOREIGN PATENT DOCUMENTS 0434571 6/1991 European Pat. Off. .

OTHER PUBLICATIONS

Marcotte, et al. "Synthesis and Evaluation of 10β-Substituted 4-Estrene-3,17-Diones as Inhibitors of Human Placental Microsomal Aromatase." *Steroids*, 39(3), Mar. 1982, pp. 325-344.
Marcotte et al., *Biochemistry*, 21, 2773 (1982).
Shih et al, *J. Chem. Soc., Chem. Commun.*, 1987, 213.
Childers et al., *J. Chem. Soc., Chem. Commun.*, 1987, 320.
Childers et al., *J. Org. Chem.*, 53, 5947 (1988).
Morrison and Boyd, "Organic Chemistry" (Boston, Allyn and Bacon 1979) pp. 564, 568, 569.

*Primary Examiner*—Marianne M. Cintins
*Assistant Examiner*—Kimberly J. Kestler
*Attorney, Agent, or Firm*—William J. Stein

[57] ABSTRACT

The present invention is directed to a group of compounds which are haloethyl substituted steroidal enzyme inhibitors. These compounds are useful as aromatase, 19-hydroxylase, and aldosterone biosynthesis inhibitors and they are prepared from the corresponding epoxide.

12 Claims, No Drawings

HALOETHYL-SUBSTITUTED STEROID ENZYME INHIBITORS

The present application is a continuation-in-part of U.S. Ser. No. 503,191, filed Apr. 2, 1990 now abandoned.

BACKGROUND OF THE INVENTION

The estrogen hormones, estrone and estradiol, which are involved in many physiological processes, are formed from cholesterol via several enzymatic steps. The enzyme aromatase is the final rate limiting enzyme in the nonreversible conversion of the androgen hormones, testosterone and androstenedione, to the estrogen hormones, estradiol and estrone. Compounds such as aromatase inhibitors may thus regulate or inhibit androgen to estrogen conversion, and have therapeutic utility in treating clinical conditions potentiated by the presence of estrogens.

19-Nordeoxycorticosterone (19-norDOC) is known to induce mineralocorticoid hypertension. In the biosynthetic formation of 19-norsteroids, such as 19-norDOC, the initial step is the adrenal $C_{19}$ hydroxylation of an appropriate steroid such as deoxycorticosterone (DOC). The inhibition of the biosynthetic formation of 19-norDOC by inhibition of 19-hydroxylation of DOC would thus serve to decrease the level of 19-norDOC present in the animal involved and reduce hypertensive effects attributable to the presence of this material.

Aldosterone is a steroidal hormone which is synthesized in the zona glomerulosa cells of the adrenal glands. The primary biological function of the compound is the regulation of salt retention. In particular, aldosterone plays a major role in controlling the reabsorption of sodium ions from the kidney filtrates. Thus, a deficiency of the enzyme responsible for the synthesis of aldosterone is a characteristic of patients with a salt-losing syndrome, while primary hyperaldosteronism can result from hyperbiosynthesis of aldosterone as caused by an adrenocortical tumor or the administration of certain drugs. The hyperaldosteronism may involve hypertension, hypokalemia, alkalosis, muscular weakness, polyuria, and polydipsia. Thus, treatment of hyperaldosteronism and the conditions associated with it would be possible by blockage of the enzymatic synthesis of aldosterone.

SUMMARY OF THE INVENTION

The present invention is directed to novel haloethyl-substituted steroidal enzyme inhibitors, their related intermediates, and the process for their preparation. These compounds may be represented by the following formulas:

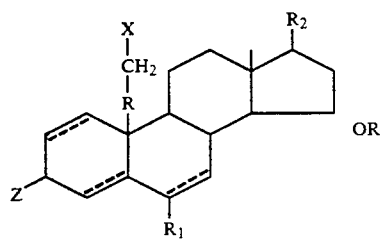

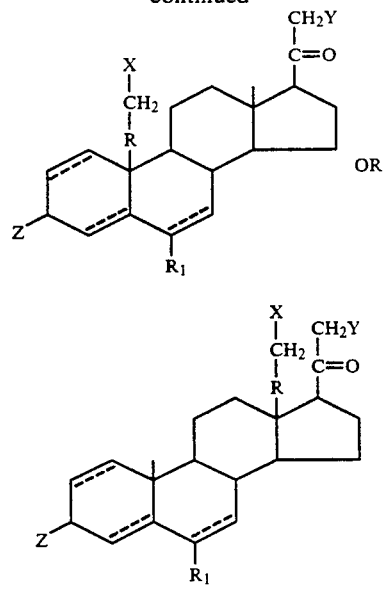

wherein
--- represents a single or double bond;
X=Br, Cl, or I;
R=CHOH or C=O;
$R_1$=H, $C_{1-4}$ alkyl, =O, or —OH;
$R_2$==O, —OH, or —O—($C_{1-4}$ alkanoyl);
Z==O, =CH$_2$, —OH, or —O—($C_{1-4}$ alkanoyl); and
Y=H, —OH, or —O—($C_{1-4}$ alkanoyl), and when Y=H, —OH, or —O—($C_{1-4}$ alkanoyl), Z may not include —OH, and $R_1$ may not include =O or —OH.

Examples of $C_{1-4}$ alkyl include methyl, ethyl, propyl, isopropyl, butyl, and isobutyl, Examples of $C_{1-4}$ alkanoyl include formyl, acetyl, propionyl, and butyryl. When R is CHOH, two optical isomers are possible. The present invention encompasses the individual pure isomers, or mixtures of the two isomers in any proportion. The (R) isomer for the halohydrin moiety at $C_{10}$ is preferred for aromatase activity. In referring to the various compounds above, the entire X—CH$_2$—R— group can be considered as the substituent in which case the first two compounds above can be considered as 10-substituted estranes and the third compound a 13-substituted gonane. Alternatively, the R carbon atom can be considered as corresponding to an angular methyl carbon in which case the three groups of compounds above can be described as 19-(X—CH$_2$— substituted) androstanes, 19-(X—CH$_2$— substituted) pregnanes and 18-(X—CH$_2$— substituted) pregnanes respectively. In this case then, the optical center which results when R is CHOH can be described as at the 19-position in the first two structures and the 18-position in the third structure.

DETAILED DESCRIPTION OF THE INVENTION

The compounds of the present invention are inhibitors of aromatase, 19-hydroxylase, and aldosterone biosynthesis. As aromatase inhibitors, they are useful in treating hyperestrogenemia. The compounds are useful in controlling abnormally high levels of estrogens, both when the high levels observed are relatively steady, or when there are brief surges of elevated levels occurring as part of cyclical body functions. Both females and males can be treated, although obviously, the level of estrogen which would be considered high in males would be much lower than the amount considered high in females. These compounds are also useful as anti-fertility agents to prevent ovulation or implantation in females, or to reduce the mating behavior in males where brain aromatization is required for such behavior. These compounds further have value in treating gynocomastia, male infertility resulting from elevated estrogen levels, and hyperestrogenemia, which may precede myocardial infarction. The compounds may also have value in the treatment of breast cancer and various estrogen-induced or estrogen-stimulated disorders, such as benign prostatic hypertrophy and endometrial hyperplasia.

The bioconversion of deoxycorticosterone via a 19-hydroxylase pathway to 19-nordeoxycorticosterone potentiates its mineralocorticoid activity. Mineralo-corticoid excess results in a syndrome characterized by hypokalemia, metabolic alkalosis, polydipsia, polyuria, and hypertensive conditions. Increased excretion of 19-nordeoxycorticosterone has been reported for hypertensive patients, including those with primary aldosteronism, Cushing's syndrome, 17α-hydroxylase deficiency, and individuals with essential hypertension. As 19-hydroxylase inhibitors, these compounds may be useful as antihypertensive agents and for management of edemous conditions often associated with sodium retention and potassium loss.

As inhibitors of aldosterone, these compounds are useful for the treatment of hyperaldosteronism and various conditions wherein a reduction of the excess amount of aldosterone responsible for the condition would be beneficial. Thus, they are useful in the treatment of hyperaldosteronism and any associated hypertension, edema, and sodium retention, whether this is a result of some bodily disorder, or whether it results from the administration of some agent. As a result of their effects on the factors responsible for edema or sodium retention, the indicated compounds would be useful in a method of treatment as diuretic agents.

To achieve their desired effect, the compounds of the present invention may be administered orally, parenterally, for example, intravenously, intraperitoneally, intramuscularly, or subcutaneously, including the injection of the active ingredient directly into tissue or tumor sites, to a patient in need of treatment. The term patient is taken to mean a warm-blooded animal, for example, mammals such as humans, primates, cattle, dogs, cats, horses, sheep, mice, rats, and pigs. These compounds may also be administered in the form of a pharmaceutical preparation, and may further be incorporated into sustained delivery devices. The amount of compound administered will vary over a wide range and be any effective amount. Depending on the patient to be treated, the condition to be treated, and mode of administration, the effective amount of compound administered will vary from about 0.01 to 150 mg/kg of body weight per day, and preferably from about 0.1 to 50 mg/kg body weight per day.

For oral administration, the compounds can be formulated into solid or liquid preparations, such as capsules, pills, tablets, troches, powders, solutions, suspensions, or emulsions. The solid unit dosage forms can be a capsule which can be of the ordinary gelatin type containing the active compound and a carrier, for example, lubricants and inert filler such a lactose, sucrose and corn starch. In another embodiment, an active compound of the invention can be tableted with conventional tablet bases such as lactose, sucrose and corn starch in combination with binders such as acacia, corn starch, or gelatin, disintegrating agents such as potato starch, or alginic acids and a lubricant such as stearic acid or magnesium stearate.

For parenteral administration the compounds may be administered as injectable dosages of a solution or suspension of the compound in a physiological acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose and related sugar solutions, ethanols and glycols, such as propylene glycol or polyethylene glycol are preferred liquid carriers, particularly for injectable solutions.

The compounds can be administered in the form of a cutaneous patch, a depot injection, or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic ®, silicone rubber manufactured by Dow Corning Corporation. Further information on suitable pharmaceutical carriers and formulation techniques are found in standard texts such as *Remington's Pharmaceutical Sciences*, Mack Publishing Company, Easton, Pa.

Inhibition of aromatase activity is demonstrated by using laboratory methods similar to procedures described in U.S. Pat. No. 4,322,416, and as published in Johnston et al., *Endocrinology* 115:776, 1984, and Burkhart et al., *Steroids* 45:357, 1985.

In this assay, the inhibitor is preincubated with enzyme prior to assaying for activity in the presence of high substrate levels. A time-related decrease in enzyme activity can be indicative of irreversible binding of the inhibitor with the enzyme.

In the time-dependent assay, an amount of the enzyme inhibitor in 100 µl of the assay buffer described above which will provide assay concentrations which are usually between 1 nM and 10 µM are added to 35 ml centrifuge tubes containing 600 µl of the NADPH generating system. The preincubation is started by the addition of 700 µl of of aromatase preparation, usually 50–800 µg of microsomal protein per ml of assay buffer. These preparations are mixed using a vortex mixer and incubated for 0, 5, 10, or 20 minutes at 25° C. Then 100 µl of androstenedione (~6.8 µM) containing 1β-$^3$H androstenedione is added in assay buffer to provide an assay concentration of substrate (0.50 µM) which is at least ten times the $K_m$ of androstenedione (0.04 µM). Following vortexing, the enzyme incubation is continued for 10 minutes before being terminated by the addition of chloroform. The amount of radioactivity in the aqueous fraction is determined by scintillation procedures. The enzymatic activity for each concentration of inhibitor at each time period of preincubation is calculated as a percent of the respective vehicle control which is arbitrarily set at 100%. Therefore, the relative enzyme inhibition is expressed as a percentage: (100 percent minus percent enzyme activity with inhibitor present).

Enzyme kinetic analysis utilized Kitz-Wilson plots for time-dependent assays. These analyses provide estimates of apparent $K_i$ of inactivation which represents the inhibitor concentration required to produce half-maximal rate of enzyme inactivation. The pseudo first-order rate constant for enzyme inactivation ($k_{cat}$) and the half-time of inactivation ($\tau_{50}$) at infinite inhibitor concentrations were determined. The ratio of $k_{cat}/K_i$ (inactivation) provides an index number which increases with increased efficiency of enzyme inactivation and increased inhibitor affinity for the enzyme active site.

The compounds listed below exhibited the following results

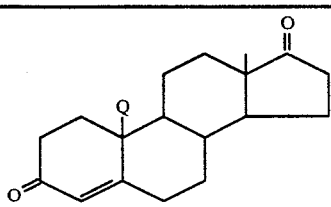

| Q | $K_i$(nM) | $\tau_{50}$(min) | $k_{cat}K_i$ |
|---|---|---|---|
| HOCHCH$_2$Br pure (S) diastereomer | 1130 | 5.33 | 1,900 |
| HOCHCH$_2$Br pure (R) diastereomer | 27 | 4.85 | 88,200 |
| O=CCH$_2$Br | 190 | 32.7 | 1,860 |
| HOCHCH$_2$Cl (R):(S): 9:1 | 63 | 3.60 | 50,700 |
| HOCHCH$_2$I (R):(S): 9:1 | 11 | 2.22 | 490,000 |

Compounds to be assayed for 11$\beta$/19-hydroxylase inhibiting activity are solubilized in dimethyl sulfoxide (DMSO) at a concentration of 10 mM and diluted with assay buffer (10 mM KCl, 1 mM EDTA, 100 mM Tris at pH 8.0) to provide the necessary concentrations. The assays are conducted in 35 ml glass tubes maintained at 25° C. in a Dubnoff shaker with 95% O$_2$/5% CO$_2$ atmosphere. The assay tubes contain the following: 100 $\mu$l of an NADPH-generating system (5 mM NADP, 15 mM glucose-6-phosphate, and 5 I.U./ml glucose-6-phosphate dehydrogenase), 300 $\mu$l of hamster adrenal mitochondrial protein, 50 $\mu$l of test compound or buffer (control), and 50 $\mu$l tritium-labeled substrate, i.e., 1 $\mu$M [$^3$H]DOC.

Compounds are evaluated for their inhibition by preincubating with the enzyme preparation supplemented with the NADPH-generating system for 0 to 60 min at 25° C. prior to the addition of radiolabeled substrate. Assays are incubated for varying time intervals from 1 to 60 min. Assays are quenched by the addition of 5 ml of ethyl acetate. Nonradiolabeled steroids are added and samples are extracted twice with 5 ml of ethyl acetate, and the solvent is evaporated under nitrogen at 30°–40° C.

The residues are redissolved in 10 mM sodium acetate:acetonitrile 1:1 v/v (pH 6.0), and high performance liquid chromatography (HPLC) is used to separate products on two C$_{18}$ Radial Pak columns (Waters, Millipore Corporation, Milford, Mass.) in series (5 $\mu$M particles, 0.8×10 cm each). Chromatographic buffer A is 10% CH$_3$CN/90% 10 mM sodium acetate (pH 6.0), and buffer B is 80% CH$_3$CN/20% 10 mM sodium acetate 9pH 6.0). The amount of remaining labeled DOC substrate and initial hydroxylated products, corticosterone and 19-hydroxy-DOC, are separated and the radioactivity contained in each peak is quantitated. The 19-hydroxylase activity is based on the quantity of radiolabeled DOC metabolized, since hamster adrenal corticosterone and 19-hydroxy-DOC are the products of a single enzyme.

Unlabeled steroids are monitored by their absorbance at 240 nm with an inline spectrometer. The extinction coefficients for derivatives of DOC are assumed to be similar to that of DOC ($\epsilon = 17,200$ M$^{-1}$cm$^{-1}$). Radioactivity of DOC metabolites is measured using an inline scintillation spectrometer with a 1 ml flow cell.

Time-dependent enzyme inhibition is evaluated by preincubating the enzyme with steroidal compound for either 0 or 60 minutes at 25° C. prior to the addition of radiolabeled substrate for a 5 minute assay. Apparent $K_m$ for the initial hydroxylation of DOC may be estimated by the double reciprocal plot of Lineweaver-Burk. IC$_{50}$'s may be graphically estimated from linear-log plots of enzyme activities and log of inhibitor concentrations.

The activity of the present compounds as aldosterone biosynthesis inhibitors can be demonstrated by the following procedure which measures the inhibition of enzymes in the synthesis of aldosterone.

Young male Sprague-Dawley rats are maintained on a sodium-deficient diet for about two weeks prior to use. From these animals, adrenal capsule/glomerulose homogenates are prepared (6 mg/ml) in pH 7.4 assay buffer [MgCl$_2$8.5 mM, CaCl$_2$ 2.7 mM, KCl 3.13 mM, NaCl 7.591 mM, TRIS 50 mM, and 0.1% triethylamine] and centrifuged 500×g for 10 minutes.

Assays are conducted in 35 ml glass tubes maintained at 25° C. in a Dubnoff Shaker with 95% O$_2$/5% CO$_2$. The tubes contain the following material: 100 $\mu$l of a NADPH generating system, 300 $\mu$l of adrenal capsular/glomerulosa cytosol, and 50 $\mu$l of test compound or buffer (control). After initial incubation intervals of 20 minutes, the 10 minute assay is started by the addition of 50 $\mu$l tritium-labelled substrate, i.e., 1 $\mu$M [$^3$H]-DOC. Reactions are quenched by the addition of 5 ml of ethyl acetate and nonradiolabelled steroids are also added. The samples are extracted twice with 5 ml of ethyl acetate and the solvent is evaporated under nitrogen at 30°–40° C.

Residues are redissolved in methanol:water (40:60) with 0.1% triethylamine and high performance liquid chromatography is used to separate products on a C18 reverse phase 5 $\mu$ ODS-Hypersil) column (4.6×250 mm, Shannon) with a 1 ml/min flow rate using a MeOH:water gradient (solvent A 10/90:solvent B 90/10). Unchanged substrate and products formed are monitored by UV absorbance at 246 nM and the amount of tritiated steroid compounds present is quantified by radioactivity measurement.

The preparation of these compounds may be illustrated by the following scheme:

Scheme 1

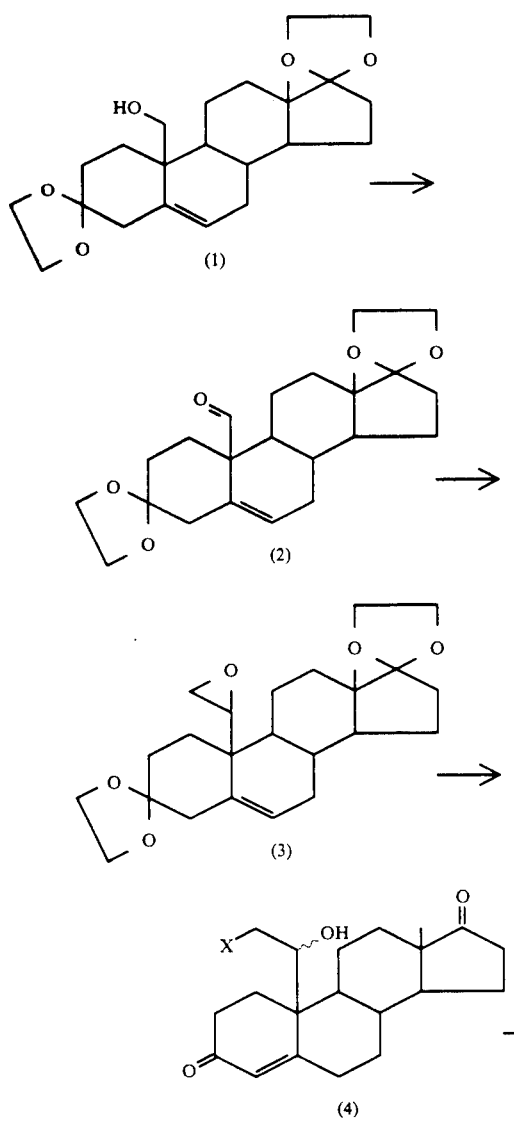

The known steroidal alcohol, 3,3:17,17-bis[1,2-ethanediylbis(oxy)]androst-5-en-19-ol (1) is reacted with dimethyl sulfoxide and oxalyl chloride in methylene chloride. $Et_3N$ is added to the resulting mixture. This mixture is treated with methylene chloride/water and the layers separated. Flash chromatography of the organic layer yields the desired steroidal aldehyde compound (2).

The steroidal aldehyde (2) is treated with sodium dimsylate and trimethylsulfonium iodide. This mixture is then added to a mixture of $Et_2O$/water and the layers separated. The organic layer yields a mixture of diastereomers of the steroidal epoxide (3). To an acetone solution of the steroidal epoxide (3) is added aqueous halo-acid (HX, wherein X=Br, Cl, or I), then methylene chloride. The organic layer yields, upon flash-chromatography, the halo-alcohol (4).

Alternatively, the bromohydrin can be obtained by using trimethylsilyl bromide. In this case, the epoxide (3) is treated with acid to remove the ketal protecting groups and give the corresponding 3,17-dione with a shift of the double bond from the 5-position to the 4-position. The resulting epoxide diketone is then reacted with trimethylsilyl bromide in an inert solvent at low temperature (about $-44°$ C.) to give the bromo trimethylsilyl ether derivative which can be hydrolyzed to give the desired bromohydrin.

To prepare the corresponding 1,4-diene compound, for example, 10-(2-bromo-1-hydroxyethyl)estr-1,4-diene-3,17-dione, a catalytic amount of acid, such as p-toluenesulfonic acid, is added to an aqueous acetone solution of the steroidal epoxide (3). The resulting mixture is added to a mixture of ethyl acetate/$NaHCO_3$. Flash chromatography of the organic layer yields the steroidal epoxide 4-enedione as a mixture of diastereomers. This product is reacted with 2,3-dichloro-5,6-dicyano-1,4-benzoquinone in dioxane, with heating, to give the corresponding epoxide 1,4-diene dione. This product is then reacted with hydrobromic acid in acetone to give 10-(2-bromo-1-hydroxyethyl)estr-1,4-diene-3,17-dione.

To prepare the corresponding 4,6-diene compound, for example, 10-(2-bromo-1-hydroxyethyl)estr-4,6-diene-3,17-dione, the corresponding epoxide 4-ene-3,17-dione is reacted with tetrachloro-1,4-benzoquinone in toluene to give the corresponding epoxide 4,6-dienedione. This product is then reacted with hydrobromic acid in acetone to give 10-(2-bromo-1-hydroxyethyl)estr-4,6-diene-3,17-dione.

To prepare the 1,4,6-triene compound, for example, 10-(2-bromo-1-hydroxyethyl)estr-1,4,6-triene-3,17-dione, the corresponding epoxide 4,6-dienedione is reacted with 2,3-dichloro-5,6-dicyano-1,4-benzoquinone in dioxane with heating to yield the corresponding epoxide 1,4,6-triene dione. This product is then reacted with hydrobromic acid in acetone to give 10-(2-bromo-1-hydroxyethyl)estr-1,4,6-triene-3,17-dione.

The halo-ketone (5) may be prepared by the oxidation of alcohol (4) according to Scheme 2, below:

Scheme 2

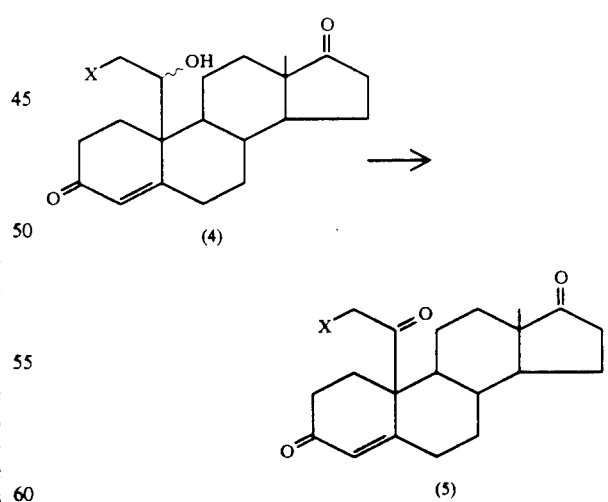

To a solution of the haloalcohol (4) in acetone is added dropwise Jones reagent ($CrO_3$/$H_2SO_4$/water). The reaction is quenched with isopropanol, diluted with methylene chloride/water, and the layers separated. Chromatography yields the haloketone (5).

To prepare compounds having the hydroxyacetyl substituent at the 17-position, Scheme 3 is utilized:

Scheme 3
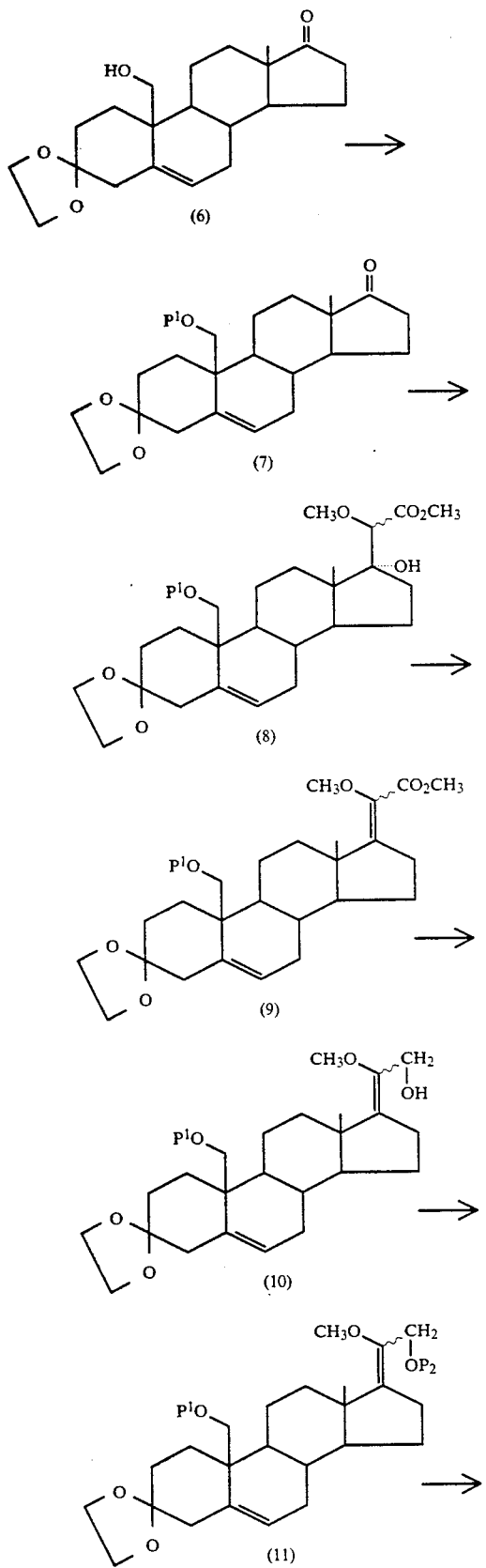
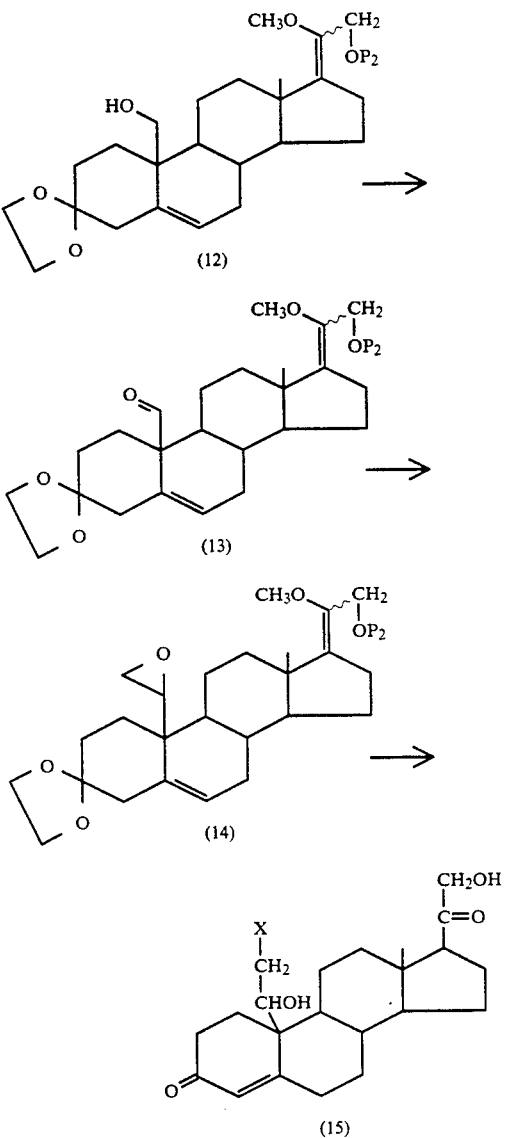
Specifically, the 21-hydroxypregnane compounds of the present invention can be prepared from the appropriate 17-keto steroid. Thus, for example, 3,3-ethylenedioxy-19-hydroxyandrost-5-en-17-one (6) is reacted with (2-chloromethoxyethyl)trimethylsilane and diisopropylethylamine in methylene chloride to give the corresponding compound (7) in which the 19-alcohol is protected by a 2-(trimethylsilyl)ethoxymethyl group. This compound is then reacted with methyl methoxyacetate and lithium diisopropylamide whereupon the indicated ester (i.e., the methylene group thereof), adds across the 17-ketone to give the 17-substituted 17-hydroxy steroid (8). Dehydration using thionyl chloride and pyridine introduces a 17-exocyclic double bond and the resulting α-methoxy ester (9) is reduced with DIBAL to the corresponding 20-methoxy alcohol (10) which is then further treated with chloromethyl methyl ether and diisopropyl amine in methylene chloride to protect the hydroxy group as the methoxymethyl ether (11). The silyl group protecting the 19-alcohol is then selectively removed by treatment with tetra(n-butyl)ammonium fluoride in tetrahydrofuran to give the 19-hydroxy compound (12). The 19-hydroxy group is then oxidized to the corresponding aldehyde (13) using a standard Swern oxidation. Reaction of the aldehyde with trimethylsulfonium iodide in dimethylsulfoxide gives the corresponding oxirane (14). Reaction of the oxirane with aqueous hydrohalic acid, e.g. hydrobromic acid, in acetone opens the oxirane ring to give the corresponding halohydrin, e.g. bromohydrin. At the same time the oxirane ring is opened, the acid used also serves to remove the protecting groups located elsewhere on the molecule. That is, the enol ether and the methoxymethyl ether that are part of the 17-substituent in the steroid are removed and the 17-hydroxyacetyl group results. In addition, the 3,3-ethylene-dioxy group is removed and the 3-keto-$\Delta^4$ compound (15) results.

To prepare those compounds wherein $R_2$ is —OH, the following scheme can be utilized:

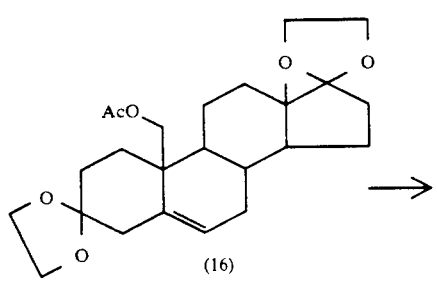

(16)

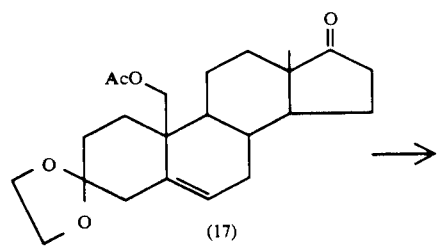

(17)

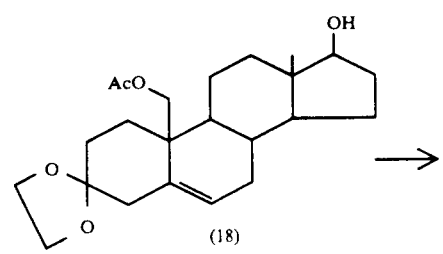

(18)

-continued

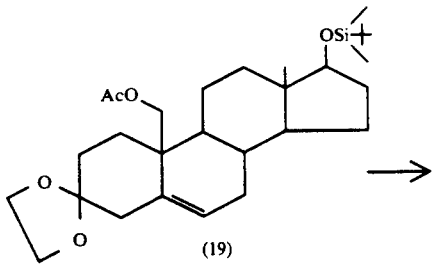

(19)

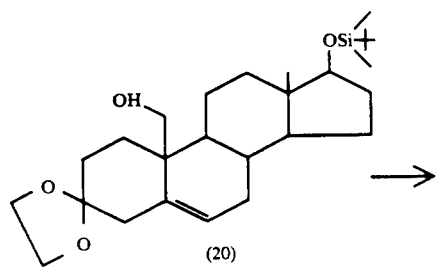

(20)

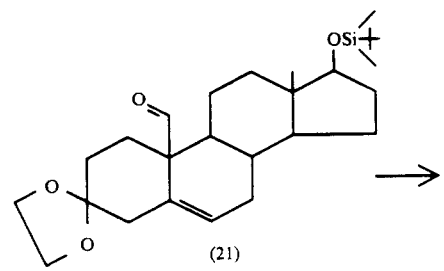

(21)

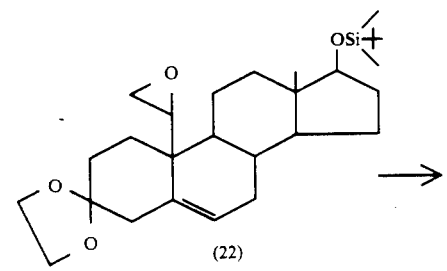

(22)

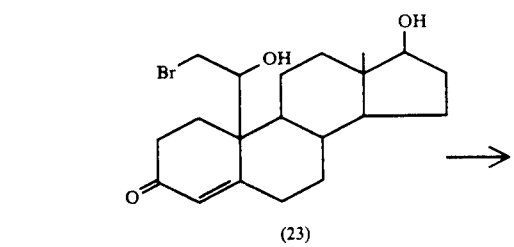

(23)

The starting compound, 19-acetoxy-3,3,17,17-bis(ethylenedioxy)androst-5-ene (16) is selectively hydrolyzed using 0.15% perchloric acid in t-butanol and methylene chloride to remove the ketal group at the 17-position and give the corresponding 17-ketone (17). The ketone function is then reduced using sodium borohydride in ethanol to give the corresponding 17β-hydroxy compound (18). The 17-hydroxy compound is then reacted with t-butyldimethylsilyl chloride in an inert solvent such as dimethylformamide in the presence of 4-dimethylaminopyridine and triethylamine to give the corresponding 17-(t-butyldimethylsilyloxy) compound (19). The 19-acetoxy group is then removed by reaction of the compound with aqueous lithium hydroxide in methanol and tetrahydrofuran to give 17β-(t-butyldimethylsilyloxy)-3,3-ethylenedioxyandrost-5-en-19-ol (20). The 19-ol is then oxidized to the corresponding aldehyde (21) using dimethyl sulfoxide and oxalyl chloride in methylene chloride followed by a tertiary amine such as triethylamine. The aldehyde is then reacted with trimethylsulfonium iodide in dimethyl sulfoxide to give the corresponding oxirane (22). The oxirane is then converted to the desired corresponding bromohydrin (23) using hydrobromic acid in acetone. The conditions used to open the oxirane ring also serve to remove the ketal protecting group at the 3-position to give 10-(2-bromo-1-hydroxyethyl)-17β-hydroxyestr-4-en-3-one (23).

The preparation of the 18-halohydrin compounds can be illustrated by the following scheme:

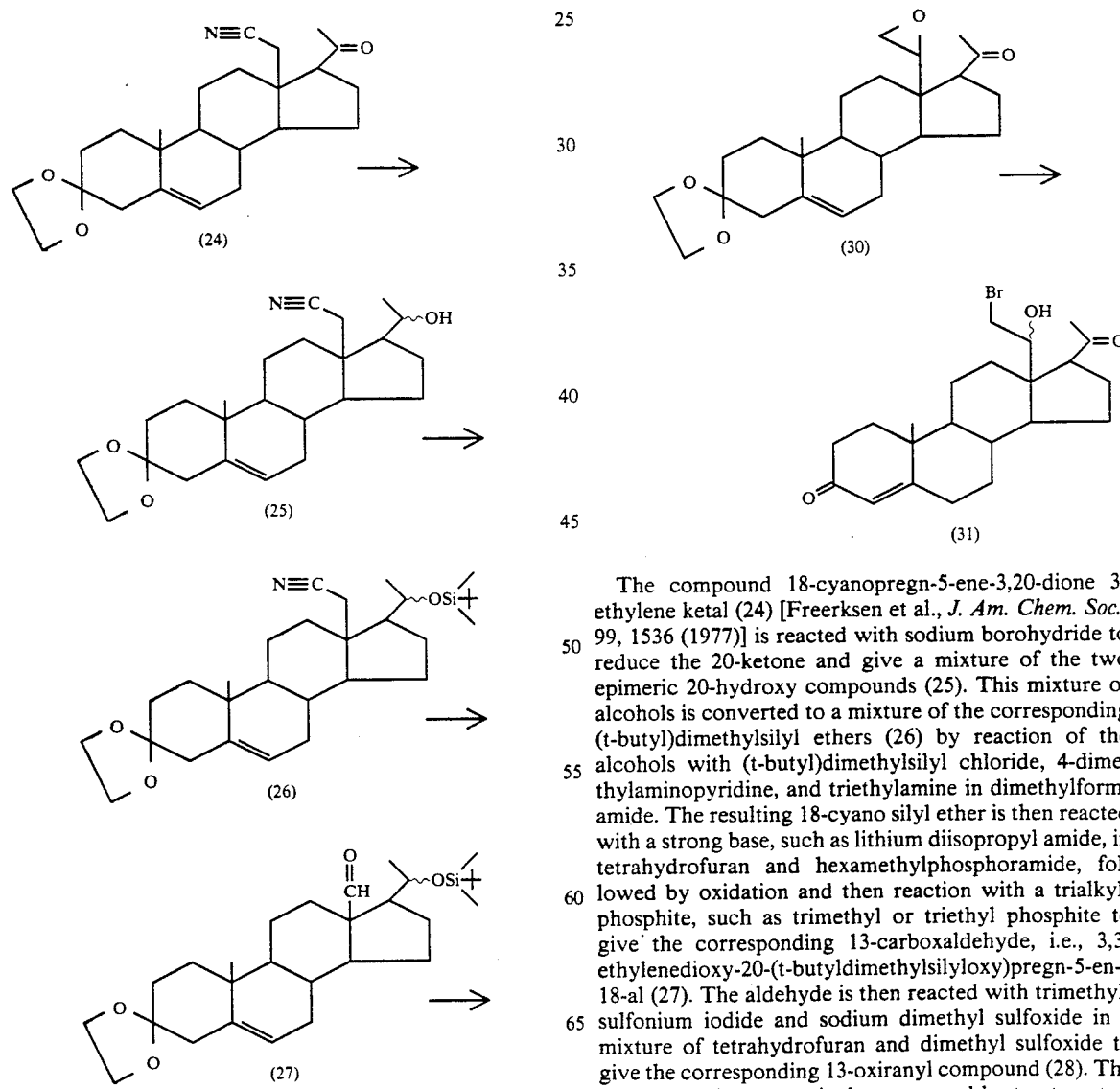

The compound 18-cyanopregn-5-ene-3,20-dione 3-ethylene ketal (24) [Freerksen et al., J. Am. Chem. Soc., 99, 1536 (1977)] is reacted with sodium borohydride to reduce the 20-ketone and give a mixture of the two epimeric 20-hydroxy compounds (25). This mixture of alcohols is converted to a mixture of the corresponding (t-butyl)dimethylsilyl ethers (26) by reaction of the alcohols with (t-butyl)dimethylsilyl chloride, 4-dimethylaminopyridine, and triethylamine in dimethylformamide. The resulting 18-cyano silyl ether is then reacted with a strong base, such as lithium diisopropyl amide, in tetrahydrofuran and hexamethylphosphoramide, followed by oxidation and then reaction with a trialkylphosphite, such as trimethyl or triethyl phosphite to give the corresponding 13-carboxaldehyde, i.e., 3,3-ethylenedioxy-20-(t-butyldimethylsilyloxy)pregn-5-en-18-al (27). The aldehyde is then reacted with trimethylsulfonium iodide and sodium dimethyl sulfoxide in a mixture of tetrahydrofuran and dimethyl sulfoxide to give the corresponding 13-oxiranyl compound (28). The silyl protecting group is then removed by treatment of the silyl ether with tetrabutylammonium fluoride to give the free 20-hydroxy compound (29) which is then subjected to a Swern oxidation to give the corresponding 20-ketone (30). The oxirane is then converted to 18-bromomethyl-18-hydroxypregn-4-ene-3,20-dione by reaction with trimethylsilyl bromide followed by dilute acid to give the bromhydrin (31). Alternatively, the oxirane (30) can be reacted with 48% hydrobromic acid in acetone to form the bromohydrin and remove the 3-ketal protecting group simultaneously, and give the desired product (31) directly. The corresponding chlorohydrin or iodohydrin may be prepared by reacting the oxirane with hydrochloric acid or hydroiodic acid, respectively.

The foregoing syntheses are illustrative, and many other conventional reactions may be used to produce or to interconvert the compounds of the invention. These conventional reactions and conditions may be found, e.g., in Fieser et al., "Steroids" (Reinhold, New York, 1959); Djerassi, Ed., "Steroid Reactions" (Holden-Day, San Francisco, 1963); Kirk et al., "Steroid Reaction Mechanisms" (Elsevier, Amsterdam, 1968); Carruthers, "Some Modern Methods of Organic Synthesis" (Cambridge U. Press, Cambridge, 1971); and Harrison et al., "Compendium of Organic Synthetic Methods" (Wiley-Interscience, New York, 1971).

Where the procedures described above give a mixture of diastereomeric halohydrins, the individual pure isomers can be obtained from the mixture by crystallization and/or chromatography by standard procedures. Alternatively, the mixture of halohydrins can be converted to the corresponding trimethylsilyl ethers using N,O-bis(trimethylsilyl)acetamide. The resulting mixture of ethers can then be separated by crystallization and/or chromatography to give the individual pure ethers which can then be converted to the pure halohydrins by treatment with acid.

The following examples are presented to illustrate the invention. They are not intended to limit the invention in any manner.

EXAMPLE 1

3,3:17,17-Bis[1,2-ethanediylbis(oxy)]androst-5-en-19-al (2)

To a stirred solution of oxalyl chloride (0.43 ml, 4.88 mmol) in methylene chloride (13 ml) under an argon atmosphere and cooled to $-55°$ C. was slowly added dimethyl sulfoxide (0.69 ml, 9.75 mmol) diluted with methylene chloride (2 ml). After 4 minutes, 3,3:17,17-bis[1,2-ethanediylbis(oxy)]androst-5-en-19-ol (1) (1.27 g, 3.25 mmol) in methylene chloride (5 ml) and dimethyl sulfoxide (0.5 ml) was slowly added. The resulting suspension was stirred at $-55°$ C. for 35 minutes, Et$_3$N (2.72 ml, 19.50 mmol) was added, the mixture was further stirred 5 minutes, and then allowed to warm to room temperature. The mixture was poured into methylene chloride (50 ml)/water (50 ml). The layers were separated and the aqueous layer was further extracted with methylene chloride (20 ml). The combined organic layers were washed with 0.5N HCl (15 ml), saturated NaHCO$_3$ (25 ml), then brine (25 ml). Drying (MgSO$_4$) and concentration gave a tan solid which was dissolved in methylene chloride (2 ml) and loaded onto a column. Flash chromatography, using ethyl acetate-hexane (35:65) as the eluant, gave the desired aldehyde, 3,3:17,17-bis[1,2-ethanediylbis(oxy)]androst-5-en-19-al (2) (1.07 g, 85% yield) as a white solid. (Melting point=168°-170° C.).

Analysis (C$_{23}$H$_{32}$O$_5$): Calculated: C, 71.11; H, 8.30. Found: C, 71.21; H, 8.40.

$^1$H-NMR: (CDCl$_3$): δ 9.69 (s, 1H, CHO), 5.81-5.87 (m, 1H, vinyl H), 3.78-4.02 (m, 8H, 2×OCH$_2$CH$_2$O), 0.79 (m, 3H, 18-CH$_3$).

MS: (EI) m/z (rel. intensity): 388 (M$^+$, 2), 360 (4), 359 (3), 298 (18), 297 (22), 253 (8), 235 (7), 99 (100).

(CI/CH$_4$) m/z (rel. intensity): 389 (MH$^+$, 100), 361 (13), 327 (20), 299 (9), 99(11).

EXAMPLE 2

10β-[(R)-Oxiranyl] and 10β-[(S)-Oxiranyl] compounds (3)

A stirred solution of sodium dimsylate (27 ml, 1.52M, 41.11 mmol) under an argon atmosphere at room temperature was diluted with tetrahydrofuran (80 ml), then cooled in an ice-salt bath. A solution of trimethylsulfonium iodide (8.39 g, 41.11 mmol) in dimethyl sulfoxide (32 ml) was slowly added. After 10 minutes, a solution of the compound of Example 1 (3.55 g, 9.14 mmol) in tetrahydrofuran (35 ml) was further added. After cooling 1 hour in an ice-salt bath, the cooling bath was removed and the mixture was allowed to warm to room temperature. After 75 minutes at room temperature, the mixture was poured into Et$_2$O (850 ml)/water (350 ml). The layers were separated and the aqueous layer was further extracted with Et$_2$O (100 ml). The combined organic layers were washed with water (2×300 ml) followed by brine (150 ml). Drying (MgSO$_4$) and concentration gave an oily foam. Crystallization from Et$_2$O-hexane gave the 10β-[(R)-oxiranyl] and 10β-[(S)-oxiranyl] compound (1.12 g, mixture of diastereomers; ratio 19R:19S::9:1). The filtrate was flash chromatographed, eluting with ethyl acetate/hexane (3:7), to give additional compound (3) (1.62 g, mixture of diastereomers; ratio 19R:19S::9:1).

Analysis (C$_{23}$H$_{34}$O$_5$): Calculated: C, 71.61; H, 8.71. Found: C, 71.67; H, 8.71.

$^1$H-NMR: (CDCl$_3$) δ 5.56-5.61 and 5.49-5.56 (pr m, 1H, vinyl H), 3.80-4.00 (m 8H, 2×OCH$_2$CH$_2$O), 3.04 and 2.95 (d and t, 1H, OCH), 2.52-2.78 (m, 3H), 0.94 and 0.86 (pr s, 3H, 18-CH$_3$).

MS: (EI) m/z (rel. intensity): 402 (M$^+$, 27), 358 (3), 99 (100).

(CI/CH$_4$) m/z (rel. intensity): 403 (MH$^+$, 100), 402 (M$^+$, 20), 401 (27), 385 (32), 373 (45), 341 (57), 323 (18), 311 (20), 99 (30).

EXAMPLE 3

10-(2-Bromo-1-hydroxyethyl)estr-4-ene-3,17-dione (4)

To a stirred solution of the compound of Example 2 (165 mg, 0.41 mmol) in 3 ml of acetone was added 0.5 ml of 48% aqueous hydrobromic acid. After 30 minutes, the reaction was diluted to 25 ml with water and poured into methylene chloride (35 ml)/water (25 ml). The layers were separated and the aqueous layer was extracted with additional methylene chloride (15 ml). The combined organics were washed with water (35 ml) followed by brine (20 ml). Drying (MgSO$_4$) and concentration gave the crude bromohydrin, 10-(2-bromo-1-hydroxyethyl)estr-4-ene-3,17-dione (4, X=Br) as an oily, white, waxy solid. This product was dissolved in methylene chloride (1 ml), loaded onto a 2×12 cm silica gel column for flash chromatography, eluted with ethyl acetate/hexane (40/60), and 15 ml fractions collected.

Fractions 8-14 were combined and concentrated to a white, waxy solid (131 mg). An $^1$H-NMR spectrum was obtained and revealed the bromohydrin as a mixture of both diastereomers with a ratio of approximately 6:1. The resulting solid of fractions 8-14 was triturated with several mls of Et$_2$O, scraped from the sides of the flask, and filtered to yield the product (103 mg).

$^1$H-NMR: (CDCl$_3$) δ 5.97 and 5.93 (pr s, 1H, vinyl H), 4.38 and 4.08-4.16 (dt and m, 1H, CHO), 3.81 and 3.50 and 3.44 and 3.41 (four dd, 2H, CH$_2$Br), 2.59 and 2.57 (pr d, 1H, OH), 0.97 and 0.96 (pr s, 3H, 18-CH$_3$). Ratio 19R:19S::9:1.

EXAMPLE 4

10-(2-Chloro-1-hydroxyethyl)estr-4-ene-3,17-dione (4)

To a stirred solution of the compound of Example 2 (0.25 g, 0.62 mmol) in 5 ml of acetone was added 1 ml of 37% aqueous hydrochloric acid solution. After 30 minutes, the reaction was diluted to 25 ml with water and transferred to a separatory funnel containing methylene chloride (50 ml)/water (40 ml). The layers were separated and the aqueous layer was extracted with additional methylene chloride (15 ml). The combined organics were washed with water (40 ml) followed by brine (20 ml). Drying and concentration gave crude chlorohydrin, 10-(2-chloro-1-hydroxyethyl)estr-4-ene-3,17-dione (4, X=Cl) as a waxy, white solid (0.20 g). This product was dissolved in methylene chloride (1 ml) and loaded onto a 2×12 cm silica gel column for flash chromatography, eluted with ethyl acetate/hexane (50:50), and 15 ml fractions collected. Fractions 5-7 were combined and concentrated to a waxy, white solid (163 mg). To this product was added 5 ml of Et$_2$O/hexane (2:1) with scraping of the sides of the flask, and the resulting white solid was then filtered and dried under high vacuum over refluxing acetone. There was slight discoloration from white solid to tan solid during heating, so heating was discontinued. The sample was then dried an additional 2 hours under high vacuum without heat.

Analysis (C$_{20}$H$_{27}$ClO$_3$): Calculated: C, 68.46; H, 7.76. Found: C, 68.27; H, 7.94.

$^1$H-NMR: (CDCl$_3$) δ 5.97 and 5.92 (pr s, 1H, vinyl H), and 4.33 and 4.09 (pr dt, 1H, CHO), 3.90 and 3.47-3.61 (dd and m, 2H, CH$_2$Cl), 2.64 and 2.62 (pr d, 1H, OH), 0.97 and 0.96 (pr s, 3H, 18-CH$_3$). Ratio 19R:19S::9:1.

MS: CI/CH$_4$ m/z (rel. intensity): 353(20), 352(17), 351(100), 315(21), 273(54).

IR: (KBr) 3456, 2956, 2932, 2882, 2854, 1738, 1664, 1616, 746, 692 cm$^{-1}$.

EXAMPLE 5

10-(2-Iodo 1 hydroxyethyl)estr-4-ene-3,17-dione (4)

To a stirred solution of the compound of Example 2 (0.25 g, 0.62 mmol) in 5 ml of acetone was added 1 ml of 50% aqueous hydroiodic acid solution. After 20 minutes, the reaction was diluted to 25 ml with water and transferred to a separatory funnel containing methylene chloride (35 ml)/water (60 ml). The layers were separated and the aqueous layer extracted with additional methylene chloride (2×10 ml). The combined organics were washed with 10% aqueous Na$_2$S$_2$O$_3$ (25 ml) followed by brine (20 ml). Drying (MgSO$_4$) and concentration gave crude iodohydrin, 10-(2-iodo-1-hydroxyethyl)estr-4-ene-3,17-dione (4, X=I) as an orange oil. To this product was added Et$_2$O and the mixture was concentrated to give a yellow solid (0.26 g). This product was dissolved in methylene chloride (1 ml) and loaded onto a 2.5×12 cm silica gel column for flash chromatography, eluted with ethyl acetate/hexane (50:50), and 15 to 20 ml fractions were collected. Fractions 6-10 were combined and concentrated to give a white solid (220 mg). To this product was added 4.5 ml of Et$_2$O/hexane (2:1) with scraping of the sides of the flask, and the resulting white solid was filtered (171 mg) and dried under high vacuum for 4 hours (166 mg).

Analysis (C$_{20}$H$_{27}$IO$_3$): Calculated: C, 54.31; H, 6.15. Found: C, 54.41; H, 6.25.

$^1$H-NMR: (CDCl$_3$) δ 5.97 and 5.93 (pr s, 1H, vinyl H), 4.40 and 4.13 (pr ddd, 1H, CHO), 3.66 and 3.20-3.40 (dd and m, 2H, CH$_2$I), 0.97 and 0.96 (pr s, 3H, 18-CH$_3$). Ratio 19R:19S::9:1.

MS: (CI/CH$_4$) m/z (rel. intensity): 443(32), 317(20), 315(30), 273(100).

IR: (KBr): 3452, 2938, 2880, 2852, 1736, 1662, 1616, 668, 638 cm$^{-1}$.

EXAMPLE 6

10-(2-Bromoacetyl)estr-4-ene-3,17-dione (5)

To a stirred solution of the compound of Example 3 (45 mg, 0.11 mmol) in 6 ml of acetone was added Jones reagent (CrO$_3$/H$_2$SO$_4$/water) dropwise until a reddish-brown color persisted for several minutes in the supernatant. Excess Jones reagent was quenched by the addition of isopropyl alcohol and the reaction was diluted with methylene chloride (35 ml)/water (50 ml). The layers were separated and the aqueous layer was extracted with additional methylene chloride (15 ml). The combined organics were washed with water (20 ml) followed by brine (15 ml). Drying (MgSO$_4$) and concentration gave crude 10-(2-bromoacetyl)estr-4-ene-3,17-dione (5) as a pale yellow oil. This product was dissolved in methylene chloride (1 ml) and loaded onto a 2×8 cm silica gel column for flash chromatography, eluted with ethyl acetate/hexane (50:50), and 15 ml fractions were collected. Fractions 5-8 were collected and concentrated to give (5) as a white foam (36 mg).

HRMS: MH$^+$ calculated for C$_{20}$H$_{25}$BrO$_3$=393.1065. MH$^+$ found=393.1045. Error=−5.0 ppm.

$^1$H-NMR (CDCl$_3$) δ 6.06 (s, 1H, vinyl H), 4.19 and 4.07 (pr d, 2H, CH$_2$Br), 0.99 (s, 3H, 18-CH$_3$).

MS: (CI/CH$_4$) m/z (rel. intensity): 395(97), 393(97), 377(13), 375(13), 343(12), 315(100), 297(16), 273(25), 272(13), 271(22).

IR: (KBr): 2940, 2856, 1736, 1674 cm$^{-1}$.

EXAMPLE 7

10β-[(R)-Oxiranyl]- and 10β[(S)-Oxiranyl]-androst-4-ene-3,17-dione

To a stirred solution of steroidal epoxide (3) (1.52 g. 3.78 mmol) in acetone (50 ml) and water (1 ml) was added p-toluenesulfonic acid monohydrate (0.18 g, 0.94 mmol). After 17 hours, the reaction mixture was concentrated to one third the original volume, poured into ethyl acetate (125 ml)/half saturated aqueous sodium bicarbonate (50 ml) and the layers separated. The aqueous layer was extracted further with ethyl acetate (30 ml) and the combined organics washed with saturated aqueous sodium bicarbonate (20 ml), water (35 ml) followed by brine (35 ml). Drying (MgSO$_4$) and concentration gave an oily, white foam which was loaded onto a column. Flash chromatography, eluting with ethyl acetate/hexane (3:2), gave a water white oil which began to solidify upon standing. Trituration with ethyl acetate (5 ml) gave the enedione (77 mg, 6.5%, mixture of two diastereomers, ratio 19R:19S::94:6) as a white solid.

1H NMR (CDCl$_3$) δ 5.91 and 5.87 (pr s 1H, vinyl H), 3.30 (dd, 1H, epoxide), 2.76 (t, 1H, epoxide), 2.59 (dd, 1H, epoxide), 0.98 and 0.95 (pr s, 3H, 18-CH$_3$).

MS (CI/CH$_4$) m/z (rel. intensity) 315(MH$^+$, 100), 297(36), 279(13).

IR (KBr) 1734, 1670, 1618 cm$^{-1}$.

Addition of hexane to the filtrate and concentration gave additional enedione (0.34 g, 28.5%, mixture of two diastereomers, ratio 19R:19S::3:1).

EXAMPLE 8

10-(2-Bromo-1-hydroxyethyl)estr-4-ene-3,17-dione (4) (using trimethylsilyl bromide)

To a stirred solution of epoxide obtained as in Example 7 (0.82 g, 2.61 mmol, ratio 19R:19S epoxide::91:9) in chloroform (25 ml) under an argon atmosphere and cooled to −44° C. was added trimethysilyl bromide (0.38 ml, 2.87 mmol). The cooling bath was removed and the solution allowed to warm to room temperature. After stirring at room temperature overnight, thin layer chromatography indicated some starting epoxide remained so the reaction was cooled to −44° C. and additional trimethylsilyl bromide (0.38 ml, 2.87 mmol) was added. The cooling bath was removed and the reaction allowed to warm to room temperature. After 3 hours, the reaction mixture was concentrated on a rotary evaporator to a yellow oil. Flash chromatography using ethyl acetate-hexane (1:1) gave the 19R-bromosilyl ether (0.26 g, 21%) as a white foam and also the 19R-bromohydrin (0.22 g, 21%). An analytical sample of the 19R-bromohydrin was obtained by trituration with ether, digesting the suspension on a steam bath for several minutes and then filtering the white solid (0.18 g).

19R-Silyl ether: 1H NMR (CDCl$_3$) δ 5.84 (s, 1H, vinyl 1 H), 4.61 (d, 1H, CHO), 3.59 and 3.20 (d and dd, 2H, CH$_2$Br), 0.94 (s, 3H, 18-CH$_3$), 0.28 [s, 9H, Si(CH$_3$)$_3$].

19R-Alcohol: mp=169°−172° C. (dec). 1H NMR (Dimethyl sulfoxide-d$_6$) δ 5.78 (s, 1H, vinyl H), 5.67 (d, 1H, OH), 4.27–4.35 (m, 1H, CHO), 3.38–3.53 (m, 2H, CH$_2$Br), 0.87 (s, 3H, 18-CH$_3$).

MS (CI/CH$_4$) m/z (rel. intensity) 397(31), 395(33), 317(22), 315(39), 301(13), 299(18), 273(100), 255(17), 125(20), 123(20).

EXAMPLE 9

[10(1R)]- and [10(1S)]-
10-(2-Bromo-1-hydroxyethyl)estr-4-ene-3,17-dione

To a stirred solution of epoxide dione (0.57 g, 1.81 mmol, 19R:19S::56:44) in chloroform (19 ml) under an argon atmosphere and cooled to −44° C. was added trimethysilyl bromide (0.26 ml, 1.99 mmol). [The particular sample of epoxide dione used was obtained from the mother liquors of an epoxide preparation as described in Example 7.] The cooling bath was removed and the reaction allowed to warm to room temperature. After stirring at room temperature overnight, the reaction was concentrated. The residue was triturated with ethyl acetate-hexane (1:1), the resultant suspension digested on a steam bath for several minutes and then suction filtered. The filtered solid was recrystallized from methylene chloride-hexane to give bromohydrin (0.10 g, mixture of diastereomers, ratio 19S:19R::9:1) as an off-white solid melting at about 183°−194° C. (dec).

1H NMR (dimethyl sulfoxide-D$_6$) δ 5.77 and 5.76 (pr s, 1H, vinyl H), 5.70 and 5.67 (pr d, 1H, OH), 4.27–4.35 and 4.03 (m and dd, 1H, CHO), 3.88 and 3.40–3.53 and 3.39 (d and m and dd, 2H, CH$_2$Br) 0.87 and 0.86 (pr s, 3H, 18-CH$_3$).

MS (CI/CH$_4$) m/z (rel. intensity) 397(52), 395(62), 379(12), 377(12), 317(16), 315(22), 273(100), 255(17), 125(10), 123(10), 85(15).

The filtrate was concentrated and loaded onto a column. Flash chromatography, eluting with ethyl acetate-hexane (1:1) gave additional bromohydrin (0.18 g, mixture of diastereomers, ratio 19R:19S::5:1).

EXAMPLE 10

[10(1R)]- and [10(1S)]-
10-[2-Bromo-1-(trimethylsilyloxy)ethyl]estr-4-ene-3,17-dione To a stirred solution of 10-(2-bromo-1-hydroxyethyl)estr-4-ene-3,17-dione (5.1 g 12.9 mmol, ratio 19R:19S::9:1) in 20 ml of anhydrous dimethylformamide under argon was added N,O-bis-(trimethylsilyl)acetamide (3.83 ml, 15.5 mmol) and the solution was stirred for 16 hours. The reaction was then diluted with methylene chloride (200 ml) and washed with water (3×100 ml) followed by brine (100 ml). The resulting solution was dried over sodium sulfate and concentrated to give a yellow oil. The oil was dissolved in ethyl acetate/hexane (35:65, 10 ml) and the solution was loaded onto a silica gel column. The column was then eluted with ethyl acetate/hexane (35:65) and various fractions were collected. The various fractions were analyzed by thin layer chromatography and the fractions were combined and concentrated. This gave [10(1R)]-10-[2-bromo-1-(trimethylsilyloxy)ethyl]estr-4-ene-3,17-dione as an oil which became a white solid (0.89 g) upon the addition of ether/hexane and concentration; and it gave [10(1S)]-10-[2-bromo-1-(trimethylsilyloxy)ethyl]estr-4-ene-3,17-dione as an oily waxy solid (0.13 g) which became a white solid upon the addition of ether/hexane and concentration.

$^1$H NMR spectra for 19S TMS ether (CDCl$_3$) δ 5.88 (s, 1H, vinyl), 4.39 (d, 1H, CHO), 3.93 and 3.38 (d and dd, 2H, CH$_2$Br), 0.97 (s, 3H, 18-CH$_3$), 0.18 [s, 9H, Si(CH$_3$)$_3$].

EXAMPLE 11

Pure
[10(1R)]-10-(2-bromo-1-hydroxyethyl)estr-4-ene-3,17-dione

To a stirred solution of [10(1R)]-10-[2-bromo-1-(trimethylsilyloxy)ethyl]estr-4-ene-3,17-dione (0.88 g, 1.88 mmol) in acetone (25 ml) was added water (1 ml) followed by three drops of 48% aqueous hydrobromic acid. After 2 hours, additional water (1 ml) and 3 drops of 48% aqueous hydrobromic acid were added and stirring was continued for an additional 3 hours. The mixture was then concentrated to about one half the original volume under reduced pressure and then water (60 ml) was added to the residue. This was extracted with methylene chloride (2×35 ml) and the combined organic extracts were washed with water (50 ml) followed by brine (30 ml). The organic solution was then dried over sodium sulfate and concentrated to give an oily solid. Addition of ether/hexane to this solid and concentration gave a white solid. This solid was dissolved in methylene chloride and chromatographed on a silica gel column using ethyl acetate/hexane (50:50) as the eluent. The appropriate fractions were then combined and concentrated to give [10(1R)]-10-(2-bromo-1-hydroxyethyl)estr-4-ene-3,17-dione as a white solid (0.69 g).

EXAMPLE 12

Pure [10(1S)]-10-(2-bromo-1-hydroxyethyl)estr-4-ene-3,17-dione

To a stirred solution of [10(1S)]-10-[2-bromo-1-(trimethylsilyloxy)ethyl]estr-4-ene-3,17-dione (0.12 g, 0.26 mmol) in acetone (5 ml) and water (0.5 ml) was added 4 drops of aqueous 48% hydrobromic acid. After 30 minutes, a precipitate began to form and additional acetone (3 ml) was added but a suspension remained. After 4.5 hours, thin layer chromatography indicated that the starting material was gone. Water (75 ml) and methylene chloride (35 ml) were added, the two layers were separated and the aqueous layer was extracted with additional methylene chloride (2×10 ml). The combined organic layers were washed with water (50 ml) followed by brine (35 ml) and then dried (sodium sulfate) and concentrated to give a white solid. This was recrystallized from a mixture of methylene chloride and hexane to give [10(1S)]-10-(2-bromo-1-hydroxyethyl)estr-4-ene-3,17-dione as a white crystalline solid (38 mg) melting at about 191°-195° C.

$^1$H NMR (CDCl$_3$) δ 5.78 (s, 1H, vinyl), 5.71 (d, 1H, OH), 4.03 (br t, 1H, CHO), 3.88 and 3.39 (d and dd, 2H, CH$_2$Br), 0.86 (s, 3H, 18CH$_3$).

IR (KBr): 3388, 1732, 1646 cm$^{-1}$.

What is claimed is:

1. A compound of the formula:

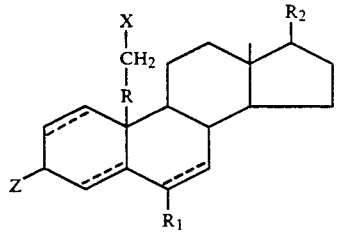

wherein

--- represents a single or double bond;
X = Br, or I;
R = CHOH or C=O;
R$_1$ = H, C$_{1-4}$ alkyl, =O, or —OH;
R$_2$ ==O, —OH, or —O—(C$_{1-4}$ alkanoyl); and
Z ==O, =CH$_2$, —OH, or —O—(C$_{1-4}$ alkanoyl).

2. A compound of the formula:

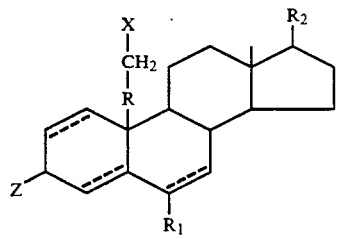

wherein

--- represents a single or double bond;
X = Br, Cl, or I;
R = CHOH;
R$_1$ = H, C$_{1-4}$ alkyl, =O, or —OH;
R$_2$ ==O, —OH, or —O—(C$_{1-4}$ alkanoyl); and
Z ==O, =CH$_2$, —OH, or —O—(C$_{1-4}$ alkanoyl).

3. A compound according to claim 2 which has the formula

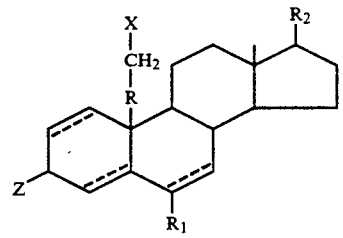

wherein

--- represents a single or double bond;
X = Br, Cl, or I;
R = CHOH;
R$_1$ = H or C$_{1-4}$ alkyl;
R$_2$ ==O or —OH; and
Z ==O, —OH, or —O—(C$_{1-4}$ alkanoyl).

4. A compound of the formula

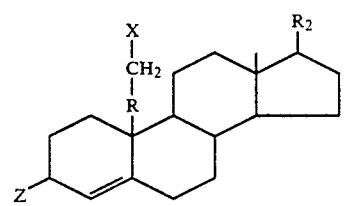

wherein

X = Br, Cl, or I;
R = CHOH;
R$_2$ ==O or —OH; and
Z ==O.

5. A compound according to claim 2 which is 10-(2-bromo-1-hydroxyethyl)estr-4-ene-3,17-dione.

6. A compound according to claim 2 which is 10-(2-chloro-1-hydroxyethyl)estr-4-ene-3,17-dione.

7. A compound according to claim 2 which is 10-(2-iodo-1-hydroxyethyl)estr-4-ene-3,17-dione.

8. The compound which is 10-(2-bromoacetyl)estr-4-ene-3,17-dione.

9. A method of inhibiting aromatase activity, which comprises contacting an effective aromatase-inhibiting amount of a compound of claim 1 with an aromatase enzyme.

10. A method according to claim 9 in which the aromatase inhibitor produces an anti-fertility effect.

11. A pharmaceutical composition suitable for the inhibition of aromatase activity which comprises an aromatase inhibiting amount of a compound of claim 1 and a pharmaceutical carrier or diluent.

12. A method of inhibiting aromatase activity, which comprises contacting an effective aromatase-inhibiting amount of a compound of claim 2 with an aromatase enzyme.

* * * * *

UNITED STATES PATENT AND TRADEMARK OFFICE
CERTIFICATE OF CORRECTION

PATENT NO. : 5,252,565
DATED : October 12, 1993
INVENTOR(S) : Peet, et. al.

It is certified that error appears in the above-indentified patent and that said Letters Patent is hereby corrected as shown below:

Title page, item [54] and col. 1, line 1, in the title, should read --
SUBSTITUTED STEROIDAL --.

Column 2, line 37, "isobutyl, Examples" should read
--isobutyl. Examples--.

Column 4, line 52, "µl of of aromatase" should read --µl of aromatase--.

Column 5, line 34, ": a:l" should read --::9:l--.

Column 6, line 59, "phase 5" should read --phase (5--.

Column 15, line 7, "bromhydrin" should read --bromohydrin--.

Column 21, line 9, "bydroxyethyl" should read --hydroxyethyl)--.

Signed and Sealed this

Ninth Day of August, 1994

Attest:

BRUCE LEHMAN

Attesting Officer     Commissioner of Patents and Trademarks